(12) United States Patent
Holdgate et al.

(10) Patent No.: US 8,961,020 B2
(45) Date of Patent: Feb. 24, 2015

(54) THRUST BEARING ASSEMBLY, DRIVE TRAIN, AND MEDICAMENT DELIVERY DEVICE

(75) Inventors: James Holdgate, Cardiff (GB); Christopher Langley, Leamington Spa (GB); Christopher Jones, Tewkesbury (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 354 days.

(21) Appl. No.: 13/384,046

(22) PCT Filed: Jul. 14, 2010

(86) PCT No.: PCT/EP2010/060126
§ 371 (c)(1),
(2), (4) Date: May 10, 2012

(87) PCT Pub. No.: WO2011/006924
PCT Pub. Date: Jan. 20, 2011

(65) Prior Publication Data
US 2012/0230620 A1    Sep. 13, 2012

(30) Foreign Application Priority Data

Jul. 15, 2009 (EP) ..................... 09009213

(51) Int. Cl.
*F16C 17/04* (2006.01)
*F16C 19/10* (2006.01)
(Continued)

(52) U.S. Cl.
CPC .............. *A61M 5/20* (2013.01); *A61M 5/14244* (2013.01); *A61M 5/14566* (2013.01); *A61M 5/31511* (2013.01); *A61M 5/31583* (2013.01)
USPC ............ 384/420; 384/590; 604/224; 74/22 R (58) Field of Classification Search
USPC .......... 384/420, 425, 590, 609, 618; 604/131, 604/207–211, 224, 228; 74/22 R, 25
See application file for complete search history.

(56) References Cited

U.S. PATENT DOCUMENTS 2,938,400 A * 5/1960 Gondek ...................... 74/424.91
3,176,963 A * 4/1965 Sturm .......................... 74/89.23
(Continued)

FOREIGN PATENT DOCUMENTS

DE        19717107        11/1998
DE      102007054019       5/2009
(Continued)

OTHER PUBLICATIONS

International Preliminary Report on Patentability for International App. No. PCT/EP2010/060126, issued Jan. 17, 2012.
(Continued)

*Primary Examiner* — James Pilkington
(74) *Attorney, Agent, or Firm* — McDonnell Boehnen Hulbert & Berghoff LLP (57) ABSTRACT

A thrust bearing assembly for guiding and driving a piston member having a lead screw for dispensing a medium of a delivery device when the piston member is driven in a first axial direction is provided. The thrust bearing assembly comprises a thrust bearing means for being integrated in the delivery device, a passageway for guiding the lead screw, and a rotary drive means for driving the lead screw and being fitted into or onto the thrust bearing means while being rotatable with regard to the thrust bearing. Further, the thrust bearing means comprises a thrust face which limits axial movement of the rotary drive means when driving the lead screw in the first axial direction. A drive train and a medicament delivery device in which the thrust bearing assembly is integrated are also provided.

8 Claims, 5 Drawing Sheets

(51) Int. Cl.
*A61M 5/315* (2006.01)
*F16H 21/00* (2006.01)
*A61M 5/20* (2006.01)
*A61M 5/142* (2006.01)
*A61M 5/145* (2006.01)

(56) References Cited

U.S. PATENT DOCUMENTS

| | | | | |
|---|---|---|---|---|
| 3,323,777 | A | * | 6/1967 | McMullen ..................... 74/441 |
| 3,778,014 | A | * | 12/1973 | Driscoll et al. ............... 384/609 |
| 4,105,098 | A | * | 8/1978 | Klimaitis ..................... 74/89.35 |
| 4,883,472 | A | | 11/1989 | Michel |
| 5,195,721 | A | * | 3/1993 | Akkerman ................... 74/89.25 |
| 5,271,286 | A | * | 12/1993 | Vranish ..................... 74/490.03 |
| 5,279,586 | A | * | 1/1994 | Balkwill ........................ 604/207 |
| 5,524,499 | A | * | 6/1996 | Joffe ............................ 74/89.36 |
| 5,611,783 | A | * | 3/1997 | Mikkelsen .................... 604/208 |
| 8,202,256 | B2 | * | 6/2012 | Moller ......................... 604/207 |
| 8,529,520 | B2 | * | 9/2013 | Daniel ......................... 604/207 |
| 2006/0151545 | A1 | | 7/2006 | Imhof et al. |
| 2011/0011191 | A1 | * | 1/2011 | Osterlaenger et al. ....... 74/89.23 |

FOREIGN PATENT DOCUMENTS

| | | |
|---|---|---|
| EP | 0143895 | 6/1985 |
| WO | 02/024260 | 3/2002 |
| WO | 03/0061736 | 7/2003 |
| WO | 2008/031235 | 3/2008 |

OTHER PUBLICATIONS

International Search Report for International App. No. PCT/EP2010/060126, completed Oct. 13, 2010.

* cited by examiner

THRUST BEARING ASSEMBLY, DRIVE TRAIN, AND MEDICAMENT DELIVERY DEVICE

CROSS REFERENCE TO RELATED APPLICATIONS

The present application is a U.S. National Phase Application pursuant to 35 U.S.C. §371 of International Application No. PCT/EP2010/060126 filed Jul. 14, 2010, which claims priority to European Patent Application No. 09009213.1 filed on Jul. 15, 2009. The entire disclosure contents of these applications are herewith incorporated by reference into the present application.

FIELD OF INVENTION

The present invention relates to a thrust bearing assembly which is particularly suitable for use in a medicament delivery device such as an injection or infusion device. Further the invention is directed to a drive train comprising the thrust bearing, and to a medicament delivery device comprising the drive train. In particular, but not exclusive, this invention has application to a medicament delivery device in which the medicament to be delivered is stored within a replaceable cartridge having a displaceable piston therein.

BACKGROUND

Such devices are, for example, commonly used by those with diabetes for the administration of insulin.

In such devices the displaceable piston is driven to cause medicament to be expelled by way of a lead screw or other piston means. The lead screw may conveniently be advanced and retracted by way of a suitable drive mechanism. It is known to provide a drive mechanism in which the rotary movement of a motor or other suitable drive means is transformed into linear movement of the lead screw.

It is also known to provide a guideway or guide housing through which the lead screw travels. However, in known devices the guideway is a separate component which is held in the desired operating position by other components of the apparatus and which increases the overall length of the medicament delivery device.

For example, in EP 0 143 895 there is disclosed an infusion device which comprises a housing having a shaped cavity formed therein. A first part of the cavity serves as a mounting support for a replaceable medicament cartridge. A rotatable driver sleeve is located in a second part of the cavity, which acts as a thrust bearing for the rotatable driver. The lead screw is adapted to travel through the driver sleeve. The threaded lead screw has opposing flat surfaces. The inside of the driver sleeve conforms to the shape of the lead screw to prevent rotation of the lead screw independently of the driver sleeve. The guideway takes the form of a threaded nut 56 threaded onto the lead screw. The nut is located in a specially shaped locating recess of the housing cavity to prevent rotation of the nut. Axial movement of the nut is prevented because in use, the nut is trapped between on one side the housing and on the other by one end of the medicament cartridge cylinder. In use, the driver sleeve carries along the threaded rod that moves ahead as a screw spindle through the nut or guideway held in the housing.

Such devices are complex to manufacture. The shaped cavity requires a suitable tolerance both correctly to receive the driver sleeve and to provide a suitably shaped locating recess for the nut acting as a guideway. In addition, correct location of the cartridge cylinder is required to prevent the nut from becoming loose and the correct location of the nut must be ensured every tune that a medicament cartridge is replaced. Such disassembly and reassembly when a cartridge is to be replaced is a disadvantage if the user, as is common amongst those with diabetes, is infirm or has impaired vision.

There is a need for a simpler and more compact arrangement for a medicament delivery device, which arrangement removes or at least reduces the above mentioned problems and which, in particular, can be used in a medicament delivery device without such an shaped cavity as described in the prior art explained above.

SUMMARY

The present invention provides a thrust bearing assembly for guiding and driving a piston member having a lead screw for dispensing a medium of a delivery device when the piston member is driven in a first axial direction. The thrust bearing assembly comprises a thrust bearing means for being integrated in the delivery device, a passageway for guiding the lead screw, and a rotary drive means for driving the lead screw and being fitted into or onto the thrust bearing means while being rotatable with regard to the thrust bearing. Further, the thrust bearing means comprises a thrust face which limits axial movement of the rotary drive means when driving the lead screw in the first axial direction.

Furthermore, according to the invention it is provided a drive train according including the thrust bearing according to the invention and a lead screw as described above, which is guided and driven by the thrust bearing assembly for dispensing a medium of a delivery device when the lead screw is driven in a first axial direction.

In addition, it is provided a medicament delivery device comprising a drive train as described above and a main housing.

Moreover, it is provided the use of a thrust bearing assembly according to the invention in a medicament delivery device.

Further, it is provided a method of assembling a medicament delivery device comprising the thrust bearing assembly according to the invention.

Further, the invention provides a method of injecting a medium by an injection device, wherein a rotary drive means is rotated with regard to a thrust bearing means into or onto which the rotary drive means is being fit, thereby driving a lead screw of the injection device in the first axial direction and dispensing a medium of a delivery device, wherein a thrust face of the thrust bearing means is limiting axial movement of the rotary drive means resulting from driving the lead screw in the first axial direction.

Preferred embodiments of the invention are described in the dependent claims.

An advantage of the invention is that in a medium delivery device, in which medium is expelled by means of moving a piston means, a simple and compact module can be provided that not only provides a thrust bearing taking the opposing force resulting from moving the piston in an expelling direction is provided, but which also fulfils the function of guiding and driving the piston means which presses the piston rod. Because of its simple and compact form, the thrust bearing assembly according to the invention can be easily adapted to special requirement that can occur because of a special configuration or circumstances in connection with a medicament delivery device.

For example, in contrast to the prior art, according to the invention it is not required to keep tolerances in a medicament delivery device housing when placing a nut in a recess of a housing as described above. In contrast, the thrust bearing device and the rotary drive means according to the invention and the give more flexibility when adjusting the motional behaviour of a piston means, for example when providing the thrust bearing assembly with a spiral coating which will be explained later in more detail, According to one aspect of the invention, the rotary drive means can be adapted for coupling a rotational movement of the rotary drive means with a rotational movement of the lead screw. The rotary drive means for driving the lead screw can be formed as a lead screw nut being adapted for engagement with a thread of the lead screw.

According to another aspect of the invention, the thrust bearing means can include a bearing surface extending along the axial direction of the delivery device when integrated therein, and the rotary drive means can include a corresponding bearing surface against the bearing surface of the thrust bearing mean.

According to still another aspect, the bearing surface of the thrust bearing means can terminate in an axial collar comprising the thrust face for limiting axial movement of the rotary drive means.

The thrust bearing assembly can also comprise an annular bearing race located between the rotary drive means and the thrust face of the thrust bearing means to provide a rotational bearing for the rotary drive means.

According to one exemplary embodiment of the invention, the passageway is designed such that it prevents rotation of the lead screw.

In this embodiment, the thrust bearing assembly can be configured such that an inner surface of the passageway and an outer surface of the lead screw are designed such that the inner surface of the passageway prevents rotation of the lead screw.

Furthermore, the inner surface of the passageway and the outer surface of the lead screw both can comprise at least one flat surface lying against each other for preventing rotation of the lead screw.

According to another embodiment of the invention, the passageway is designed such that it allows rotation of the lead screw wherein a prevention means is provided for limiting the rotational movement of the lead screw with regard to the thrust bearing means.

In such an embodiment, the prevention means can be configured such the the prevention means connects the lead screw and a housing means. The prevention means can be designed such that it allows a rotational movement of the lead screw with regard to the thrust bearing means of maximum a full revolution of the lead screw, when the lead screw is moved from a fully retracted position to a fully extended position.

According to one aspect of this embodiment of the invention, an inner surface of the passageway can comprise a spiral coating keyed to the lead screw for rotationally adjusting the lead screw in dependence of the axial position of the same.

According to an example of the invention that the rotary drive means can run on the outside of the thrust bearing, which permits a reduction in diameter of the thrust bearing and a reduction in length and diameter of the device in which it is to be mounted. The reduction in diameter of the thrust bearing improves the efficiency of the device, in terms of power consumption and this is particularly important where the device is to be powered by a battery. There is also the advantage that there is a cost saving in materials, since the thrust bearing is made of a relatively expensive material and also there is a reduced number of components and improved ease of assembly.

According to an example of the invention a thrust bearing assembly for guiding and driving a piston member having a lead screw for dispensing a medium of a delivery device when the piston member is driven in a first axial direction is provided, the thrust bearing assembly comprising:
 a thrust bearing means for being integrated in the delivery device and comprising a passageway for guiding the lead screw, and
 a rotary drive means for driving the lead screw and being fitted into or onto the thrust bearing means while being rotatable with regard to the thrust bearing,
 wherein the thrust bearing means comprises a thrust face which limits axial movement of the rotary drive means when driving the lead screw in the first axial direction.

According to an example of the invention, the rotary drive means is adapted for coupling a rotational movement of the rotary drive means with a rotational movement of the lead screw. The rotary drive means for driving the lead screw can be formed as a lead screw nut being adapted for engagement with a thread of the lead screw.

According to an example of the invention, the thrust bearing means comprises a bearing surface extending along the axial direction of the delivery device when integrated therein. Also the rotary drive means can comprise a corresponding bearing surface against the bearing surface of the thrust bearing mean.

According to an example of the invention, the bearing surface of the thrust bearing means terminates in an axial collar comprising the thrust face for limiting axial movement of the rotary drive means.

According to another example of the invention the thrust bearing assembly further comprises an annular bearing race located between the rotary drive means and the thrust face of the thrust bearing means to provide a rotational bearing for the rotary drive means.

Generally according to the invention, the piston means can be a piston rod. Further, the piston means comprises a piston rod and a piston which is formed as one piece together with the piston rod. In particular, the piston means can be formed as a L-shaped means comprising a longitudinal part forming the piston rod and a foot part forming the piston.

According to an example of the invention, an inner surface of the passageway and an outer surface of the lead screw are designed such that the inner surface of the passageway prevents rotation of the lead screw. In this regard, the inner surface of the passageway and the outer surface of the lead screw both can comprise at least one flat surface lying against each other for preventing rotation of the lead screw.

According to an alternative example of the invention, an inner surface of the passageway and an outer surface of the lead screw are designed such that they allow rotation of the lead screw for adjusting the axial movement of the lead screw when it is driven by the rotary drive means. In this regard, the inner surface of the passageway and an outer surface of the lead screw can be designed such that they allow rotation of the lead screw of maximum two full revolutions of the lead screw, when the lead screw is moved from a fully retracted position to a fully extended position by the rotary drive means. Further, an inner surface of the passageway can comprise a spiral coating keyed to the lead screw for rotationally adjusting the lead screw in dependence of the axial position of the same.

In these embodiments of the invention, generally the features of the thrust bearing of this invention and a telescopic drive mechanism can be combined.

According to another aspect of the invention, a drive train comprising the thrust bearing assembly according to an embodiment of the invention is provided, wherein the lead screw thereof is guided and driven by the thrust bearing assembly for dispensing a medium of a delivery device when the lead screw is driven in a first axial direction.

According to another aspect of the invention, the use of a thrust bearing assembly according to an embodiment of the invention in a medicament delivery device is provided.

According to another aspect of the invention, a method of assembling a medicament delivery device comprising the thrust bearing assembly according to an embodiment of the invention is provided.

According to another aspect of the invention, a method of injecting a medium by an injection device is provided, wherein a rotary drive means is rotated with regard to a thrust bearing means into or onto which the rotary drive means is being fit, thereby driving a piston member of the injection device in the first axial direction and dispensing a medium of a delivery device, wherein a thrust face of the thrust bearing means is limiting axial movement of the rotary drive means resulting from driving the piston member in the first axial direction or allowing only rotation for adjusting the axial movement of the piston member resulting from driving the piston member in the first axial direction.

BRIEF DESCRIPTION OF THE FIGURES

The invention will now be described, by way of example only, with reference to the accompanying drawings in which.

In the following detailed description, functionally equivalent components which are common to the embodiments described in connection with the Figures bear the same reference numerals, wherein repetition in describing such same components is avoided as possible.

DETAILED DESCRIPTION

Figure 1:
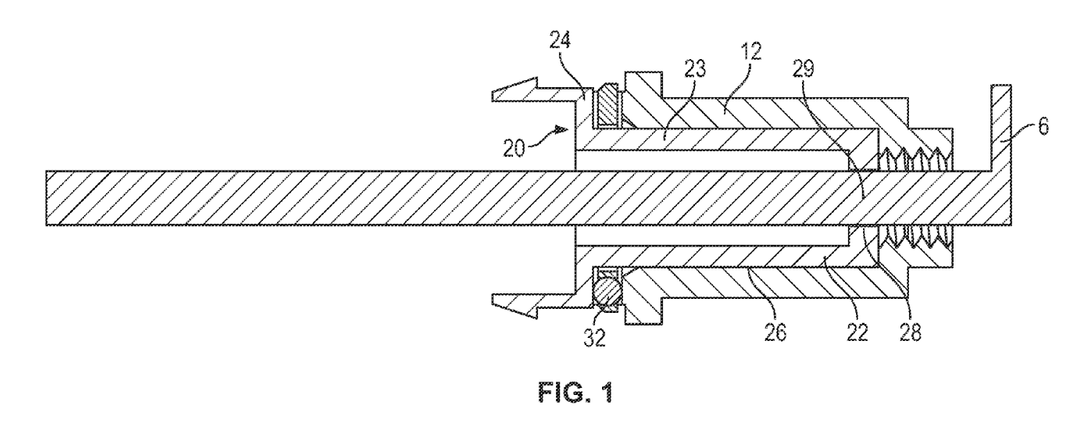
FIG. 1 shows a medicament infusion device according to an embodiment of the invention, including a thrust bearing and a rotary drive means.

Referring to the FIG. 1, there is shown a thrust bearing assembly according to an embodiment of the invention, including a thrust bearing 22 and a rotary drive means 12. The rotary drive means is coupled to a piston means comprising a lead screw 6.

Figure 2:
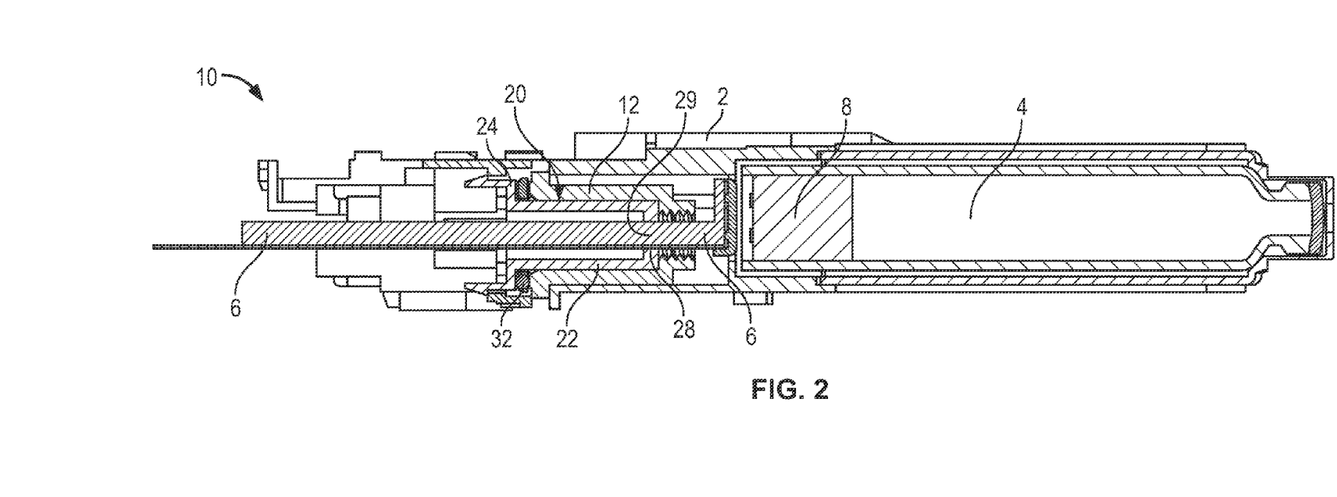
FIG. 2 shows an exemplary schematic view of a thrust bearing assembly in accordance with the present invention with the threaded lead screw also shown.
Figure 3:
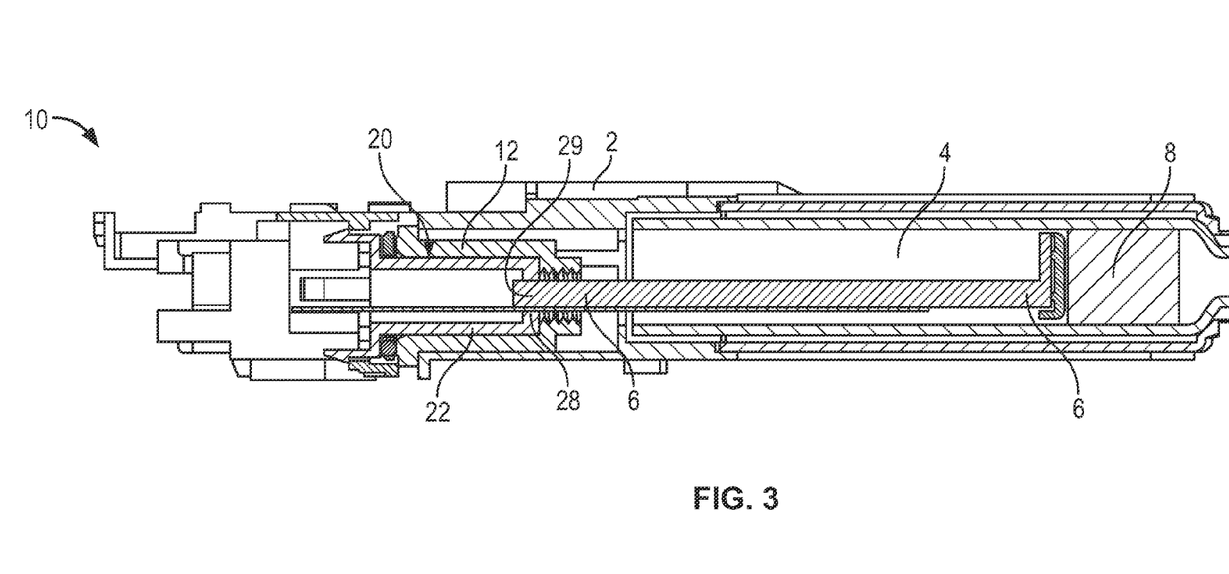
FIG. 3 shows a view of a medicament delivery device an embodiment of the thrust bearing assembly according to the invention, with the lead screw in a withdrawn position.
Figure 4:
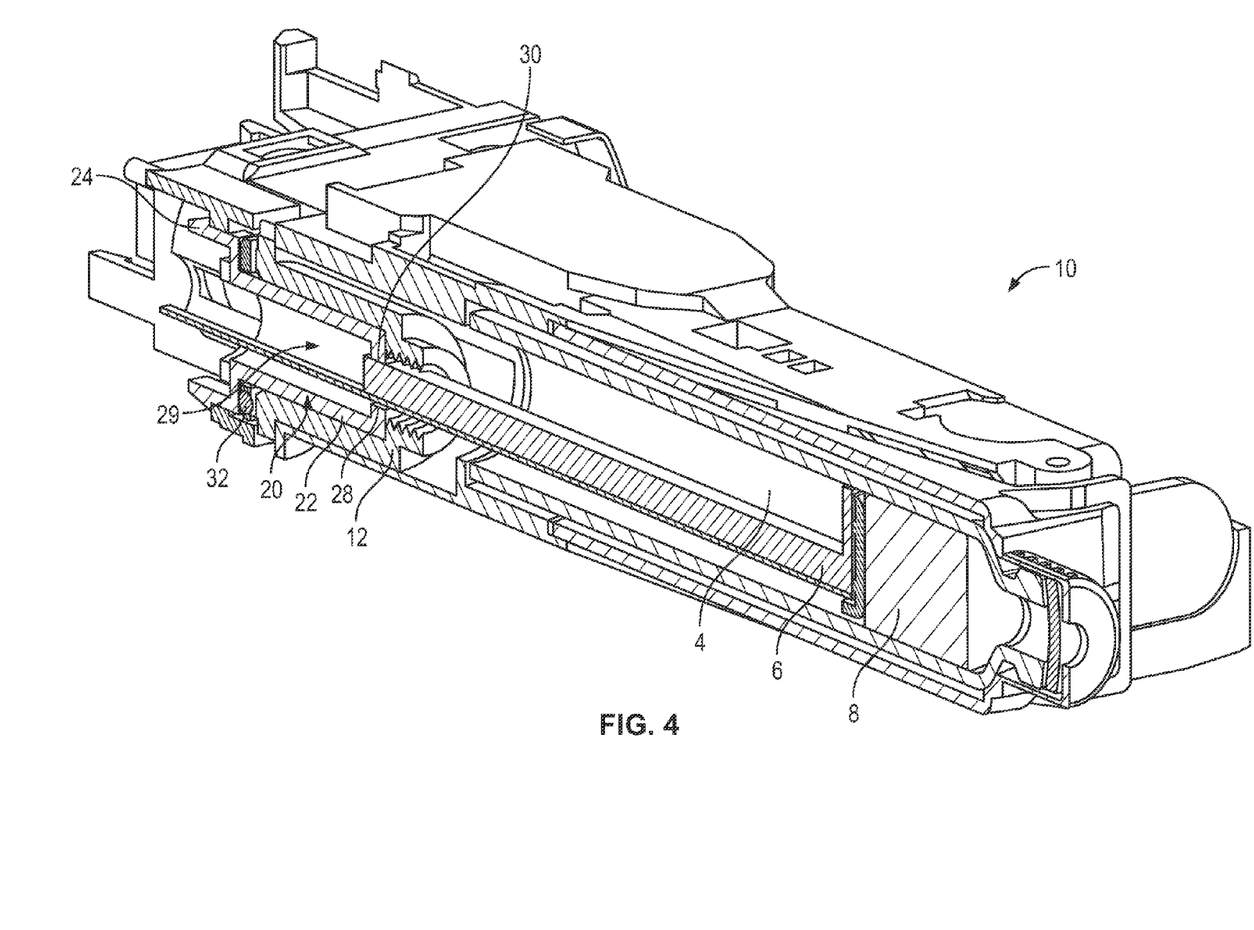
FIG. 4 shows a view of a medicament delivery device including an embodiment of the thrust bearing assembly according to the invention, with the lead screw in an extended position.

The lead screw 6 is for driving a piston 8, as is shown most clearly in FIGS. 2 to 4. In FIG. 1, the piston means is formed as a L-shaped means comprising a longitudinal part forming the lead screw 6 and a foot part forming the piston. However, alternatively, the piston means can comprise a symmetrically placed foot part as shown in FIGS. 6 to 9.

In the embodiment shown in FIG. 1, the rotary drive is configured as a lead screw nut 12. However, the form of the rotary drive means is not limited to such a form. For example, in an alternative embodiment, the rotary drive means can be coupled to the lead screw 6 by means of frictional coupling.

The thrust bearing 22 includes an inner wall surface 28 forming a passageway 29 for guiding the lead screw 6. In the embodiment shown in FIG. 1, the lead screw 6 has a non circular cross section, wherein the passageway 29 of the thrust bearing 20 is keyed to lead screw 6 and wherein the rotary drive means 12, which is configured as a lead screw nut 12, is in threaded engagement with the lead screw 6. The passageway 29 can be formed as a flat inner surface forming a guideway 30 for the threaded lead screw 6, as shown, for example, in FIG. 4. In such a configuration, the guideway 30 is configured to the cross-section of the lead screw 6 to prevent relative rotation between the lead screw 6 and the guideway 30. However, in an alternative embodiment, the thrust bearing means 20 can be in threaded engagement with the lead screw 6, wherein the rotary drive means 12 is not in threaded engagement but is keyed with the lead screw 6.

As also shown in FIG. 1, the thrust bearing means 20 supports the lead screw nut 12 and comprises a bearing surface 26, providing a bearing surface for the lead screw nut 12. The bearing surface 26 extends, when the thrust bearing means is integrated in a medicament delivery device 10 along in axial direction of the medicament delivery device 10, as shown in FIGS. 2 to 5. Correspondingly, the lead screw nut 12 comprises a corresponding bearing surface against the bearing surface 26 of the thrust bearing means.

Although in the embodiment shown in FIG. 1, the rotary drive means 12 is configured to be fitted onto the thrust bearing means 20, which is configured as an inner bushing bearing the rotary drive means 12, wherein the bearing surface 26 as an outer wall surface 26 of the thrust bearing means, the thrust bearing assembly according to the invention is not limited to such a configuration. Alternatively, the thrust bearing can be configured as an outer shell, wherein the rotary drive means is fitted into the outer shell, which is the thrust bearing.

The thrust bearing 20, which supports the lead screw nut 12, comprises a substantially cylindrical portion 23 terminating in a radial collar 24. An annular bearing race 32 is located on the collar 24 of the thrust bearing 20 to provide a thrust bearing surface for the lead screw nut 12. According to another embodiment, the rotary drive means adjoins directly to the radial collar 24 of the thrust bearing means 20, without an annular bearing race placed there between. However, an annular bearing race 32 can provide a better tendency to slide for the rotary drive means 12, when the thrust bearing assembly is in operation status and the rotary drive means rotates on the thrust bearing means 20.

Figure 5:
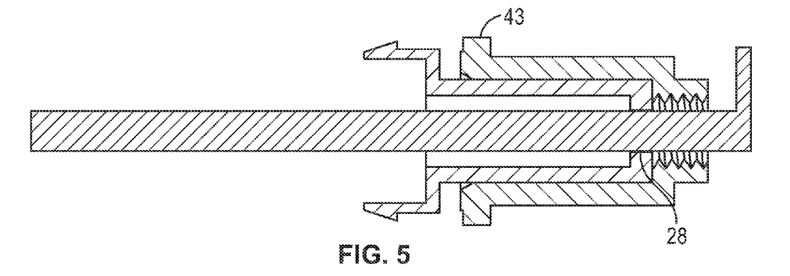
FIG. 5 shows a three quarter view corresponding to FIG. 4

An example how the piston means or lead screw 6 is driven by the lead screw nut 12 can be seen most clearly from FIGS. 3 to 5, which show the thrust bearing assembly according to the invention build in a medicament delivery device 10. According to the example shown in FIGS. 3 to 5, a medicament delivery device 10 comprises a main housing 2 within which are located a number of components including a replaceable medicament cartridge 4, a piston means in the form of a lead screw 6 to drive a piston 8 within the medicament cartridge 4 to cause in use the medicament to be expelled, and drive means in the form of a lead screw nut 12 to drive the piston means. A power source (not shown) may also be provided to power the drive means. The medicament delivery device 10 may also include a display by which certain information relevant to the operation and/or use of the medicament delivery device may be communicated to a user.

A central control unit or microprocessor (not shown) may also be provided to control operation of the medicament delivery device 10 and to determine the nature of the information appearing upon the display.

A motor (not shown) is connected via a drive train including the lead screw nut 12 and further drive elements (not shown) to drive the lead screw 6. The lead screw 6 is typically of generally circular section though having oppositely disposed flat sides extending axially of the lead screw. The remaining sides of the lead screw 6 carry a screw thread 18.

The thrust bearing 20 supports the lead screw nut 12, and comprises the substantially cylindrical portion 23 terminating in the radial collar 24. The bearing 20 includes an outer wall surface 26 providing a bearing surface for the lead screw nut 12 and opposing flat inner wall surface 28 are forming the guideway 30 for the threaded lead screw 6.

According to the example shown, the guideway 30 is configured to the cross-section of the lead screw 6 to prevent relative rotation between the lead screw 6 and the guideway 30, wherein the lead screw nut 12 is permitted to rotate with respect to the lead screw 6. When driven by the other elements in the drive train, rotation of the lead screw nut 12 in the drive train causes the lead screw 6, which is unable to rotate due to the guideway 30, to process therethrough. In this way by controlling the direction of rotation of the lead screw nut 12, the lead screw 6 may either be advanced within the replaceable medicament cartridge 4 to dispel medicament or retracted to facilitate the subsequent insertion of a replacement medicament cartridge 4.

Figure 6:
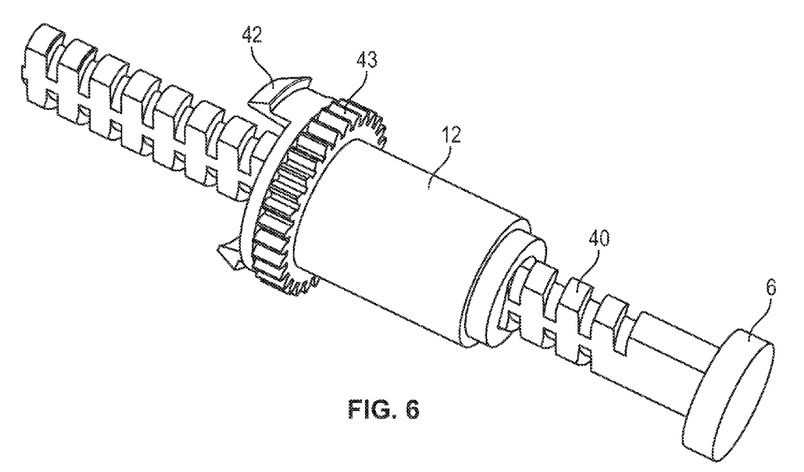
FIG. 6 shows a detailed perspective view of an embodiment of the thrust bearing assembly according to the invention.
Figure 7:
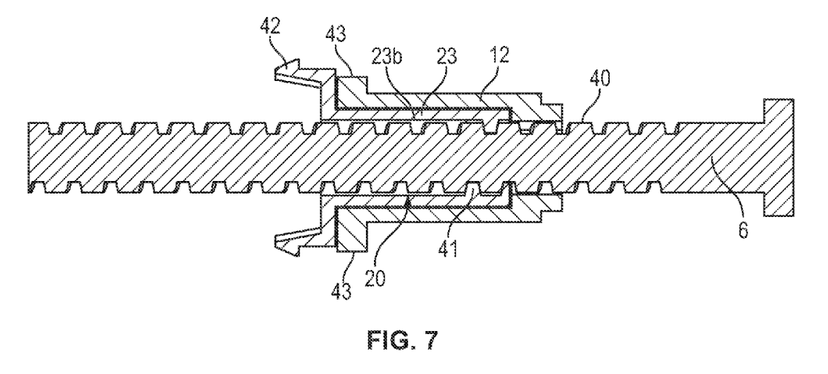
FIG. 7 shows a sectional view of the embodiment of the thrust bearing assembly according to FIG. 6.

Now referring to FIGS. 6 and 7, a first embodiment of the thrust bearing assembly according to the invention is shown in more detail. As can be seen from FIGS. 6 and 7, the lead screw 6 driven by the rotary drive means is of non-circular cross section and comprise a outer thread 40, which is in threaded engagement of an inner thread 41 provided on the inner wall of the thrust bearing means 20. Therefore, according to this first embodiment, the lead screw 6 is in threaded engagement with the thrust bearing 20. Since the inner walls of rotary drive means 12 form a non-circular cross section corresponding to the cross section of the lead screw 6, the rotary drive means is keyed to the lead screw 6. Therefore, the lead screw 6 is not allowed to rotate with regard to the rotary drive means 12. Further, since the thrust bearing means 20 and the lead screw 6 are in threaded engagement with each other, the lead screw 6 can be driven in an axial direction when the thrust bearing assembly implemented in a medicament delivery device is in operation. For provide such a function, the thrust bearing means is to be non rotatable fixed in the medicament delivery device. For this reason, the thrust bearing 20 include clip means 42 for non rotatable fixation of the thrust bearing means 20 within a housing 2 of a medicament delivery device. Please note, that the inner wall 28 of the thrust bearing shown in FIGS. 6 and 7 functions as a passageway guiding the lead screw 6 in axial direction when the lead screw 6 is driven by the rotary drive means 12.

Further, the rotary drive means comprise an outer geared ring 43 for connection with parts of a drive train to rotate the rotary drive means and, by rotating the rotary drive means 12, driving the lead screw 6. The rotation of the rotary drive means 12 can be accomplished by a motor (not shown) connected with the geared ring 43 of the rotary drive means 12. Alternatively, the rotation of the rotary drive means 12 can be accomplished in a manually manner, for example, when the rotary drive means 12 is coupled with an part of an outer housing of a medicament delivery device, which outer housing part is rotatable manually by a user. In this regard, please not that the rotary drive means according to the invention is not limited to a rotary drive means driven via a geared ring. For example, the rotary drive means can be directly connected with a rotatable housing part of a housing of a medicament delivery device. As another alternative, the rotary drive means 12 can comprise on outer frictional coupling part.

Figure 8:
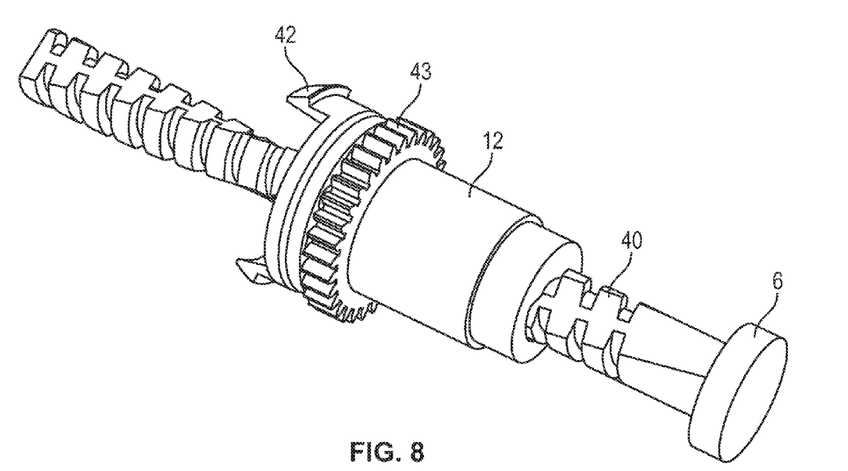
FIG. 8 shows a perspective view of a further embodiment of the thrust bearing assembly according to the invention.
Figure 9:
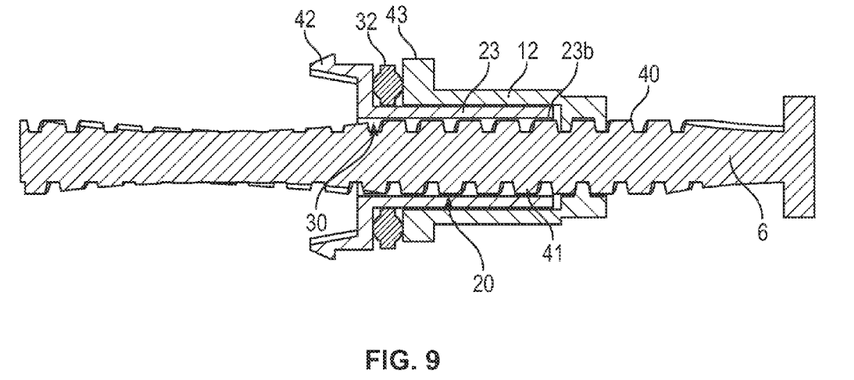
FIG. 9 shows a sectional view of the embodiment of the thrust bearing assembly according to FIG. 8.

Now referring to FIGS. 8 and 9, a second embodiment of the thrust bearing assembly is shown in more detail. The lead screw 6 is in threaded engagement with the rotary drive means 12. Further, the inner wall of the thrust bearing 20 is configured as a guideway 30 such that the thrust bearing 20 is keyed to the lead screw 6. As can be seen from FIGS. 8 and 9, the thrust bearing device according to the second embodiment is in comparison to the first embodiment shown in FIGS. 6 and 7 adapted to drive a lead screw 6 which has the form of a spiral. Therefore, the guideway 30 provided by the thrust bearing means 20 is formed such that the guideway 30 is keyed to the lead screw 6 along a twisted path. According to one embodiment of the invention, the thrust bearing 20 can comprise a spiral coating forming the twisted guideway path 30 guiding the spiral lead screw 6. According to the second embodiment, when the rotary drive means 12 is rotated, the lead screw 6 is processed in axial direction guided along the guideway 30. Because of the spiral form of the lead screw 6 and the twisted guideway 30, the lead screw 6 is performing a rotational movement along its longitudinal axis when the lead screw 6 is processed in axial direction. Therefore, according to the second embodiment, the lead screw 6 can be rotational adjusted in dependence of the axial position of the same.

While the thrust bearing according to the invention has been specifically described in relation to a thrust bearing for a medicament delivery device, it will be appreciated that it is also of more general application, in particular for application where the properties of reduced size and improved guidance for the lead screw are of significance.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin;

Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative; or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(0)14, Trp(02)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A thrust bearing assembly for guiding and driving a piston member, wherein the thrust bearing assembly comprises the piston member having a rotating lead screw configured to dispense medicament from a delivery device when the piston member is driven in a first axial direction, the thrust bearing assembly comprising:
   a thrust bearing comprising a passageway having an inner spiral coating surface keyed to the lead screw for rotationally adjusting the lead screw; and
   a rotary drive threadedly engaged to the lead screw and configured to drive the lead screw, the rotary drive is connected to the thrust bearing while being rotatable relative to the thrust bearing,
   wherein the thrust bearing further comprises a thrust face which limits axial movement of the rotary drive when driving the lead screw in the first axial direction.

2. A thrust bearing assembly according to claim 1, wherein the rotary drive for driving the lead screw is formed as a lead screw nut being adapted for engagement with a thread of the lead screw.

3. A thrust bearing assembly according to claim 1,
   wherein the thrust bearing comprises a bearing surface extending along the axial direction of the delivery device when integrated therein, and
   wherein the rotary drive comprises a corresponding bearing surface against the bearing surface of the thrust bearing.

4. A thrust bearing assembly according to claim 3, wherein the bearing surface of the thrust bearing terminates in an axial collar comprising the thrust face for limiting axial movement of the rotary drive.

5. A thrust bearing assembly according to claim 1, wherein the thrust bearing assembly further comprises an annular bearing race located between the rotary drive and the thrust face of the thrust bearing to provide a rotational bearing for the rotary drive.

6. A thrust bearing assembly according to claim 1, wherein the piston member is formed as an L-shaped rod comprising a longitudinal part forming the lead screw and a foot part.

7. A thrust bearing assembly according to claim 1, wherein the inner surface of the passageway and an outer surface of the lead screw are configured to allow a maximum of two full revolutions of the lead screw when the lead screw is moved from a fully retracted position to a fully extended position by the rotary drive.

8. A drive train comprising the thrust bearing assembly according to claim 1 and the lead screw which is guided and driven by the thrust bearing assembly for dispensing a medium of a delivery device when the lead screw is driven in a first axial direction.

* * * * *